United States Patent [19]
Kelman

[11] Patent Number: 4,932,971
[45] Date of Patent: Jun. 12, 1990

[54] CLIP-ON OPTIC ASSEMBLY

[76] Inventor: Charles D. Kelman, 721 Fifth Ave., New York, N.Y. 10022

[21] Appl. No.: 362,029

[22] Filed: Jun. 5, 1989

[51] Int. Cl.⁵ .............................................. A61F 2/16
[52] U.S. Cl. .................................................... 623/6
[58] Field of Search ............................................ 623/6

[56] References Cited

U.S. PATENT DOCUMENTS

| | | | |
|---|---|---|---|
| 4,074,368 | 2/1978 | Levy, Jr. et al. | 623/6 |
| 4,253,199 | 3/1981 | Banko | 623/6 |
| 4,409,691 | 10/1983 | Levy | 623/6 |
| 4,581,031 | 4/1986 | Koziol et al. | 623/6 |
| 4,585,455 | 4/1986 | Blackmore et al. | 623/6 |
| 4,636,211 | 1/1987 | Nielsen et al. | 623/6 |
| 4,666,446 | 5/1987 | Koziol et al. | 623/6 |
| 4,685,922 | 8/1987 | Peyman | 623/6 |
| 4,769,035 | 9/1988 | Kelman | 623/6 |

Primary Examiner—Ronald L. Frinks
Attorney, Agent, or Firm—Darby & Darby

[57] ABSTRACT

Clip-on optic assembly for clipping in situ onto a previously implanted intraocular lens to change its optical characteristics without removal from the eye, comprising a lens body having a plurality of spaced apart resilient clip members extending therefrom and outwardly terminating in clips for gripping the implanted lens peripheral edge to clip the assembly thereon. At least one clip is formed as a bent end sufficiently resilient for temporary unbending and displacement over and across the implanted lens peripheral edge to grip the clip thereon, e.g. with the clips being of selected length for maintaining the lens body optical axis concentric or eccentric to the implanted lens optical axis, the assembly upon insertion into the eye being clipped onto the implanted lens such that a bent end clip is last manipulated onto such peripheral edge.

27 Claims, 2 Drawing Sheets

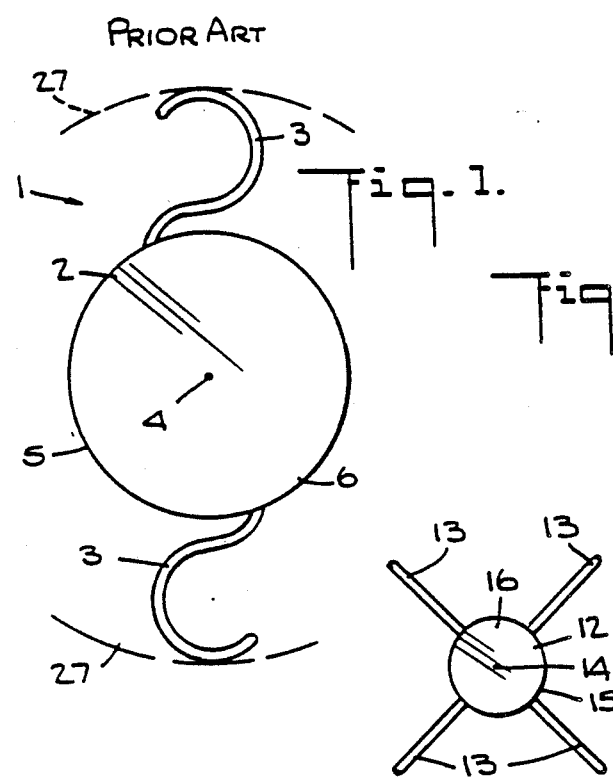
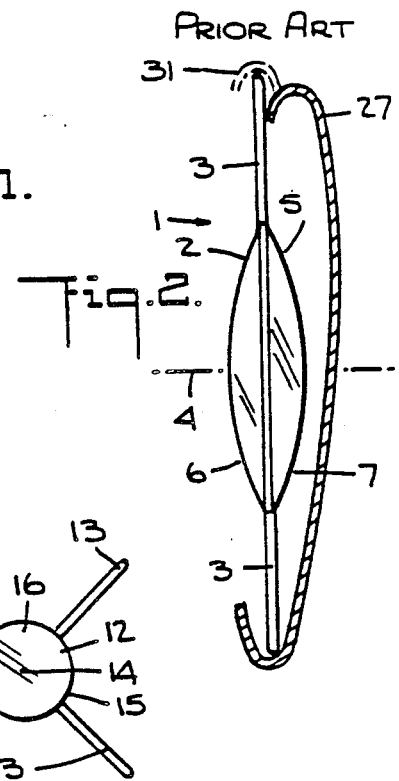
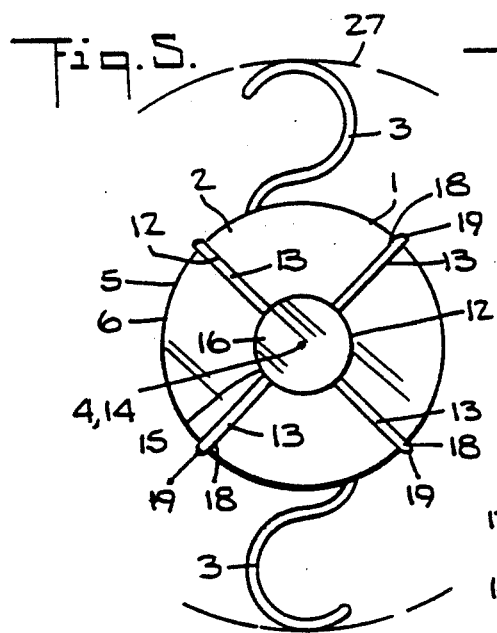
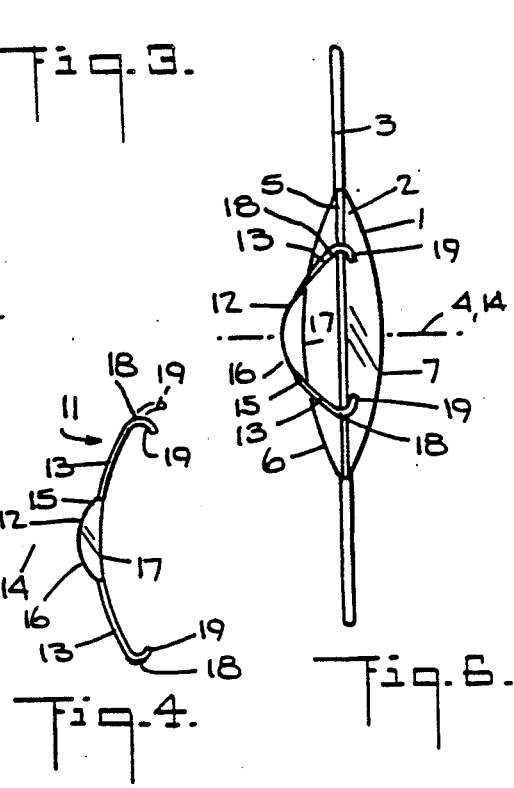

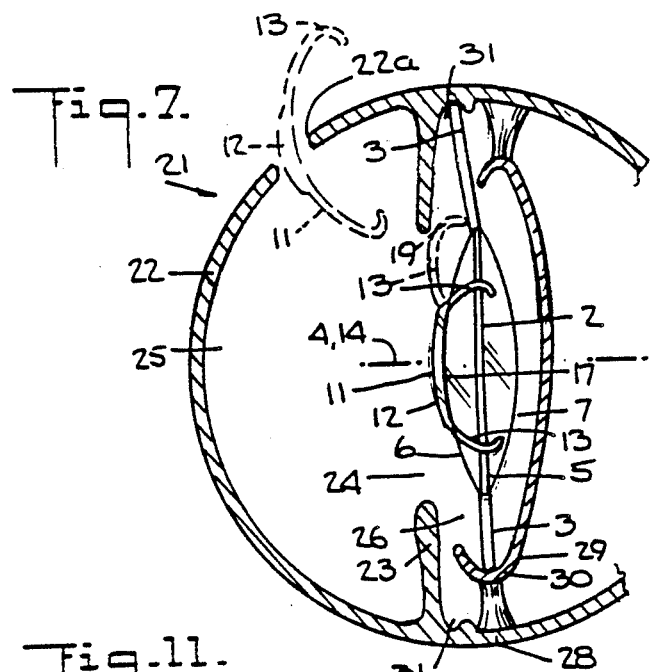
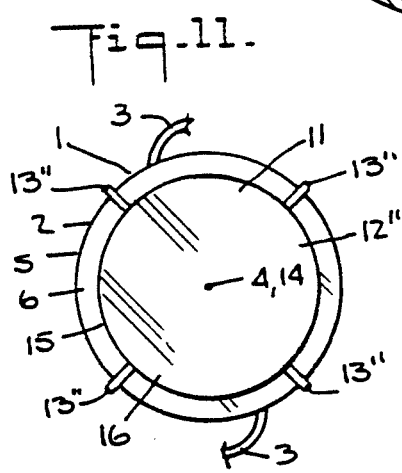
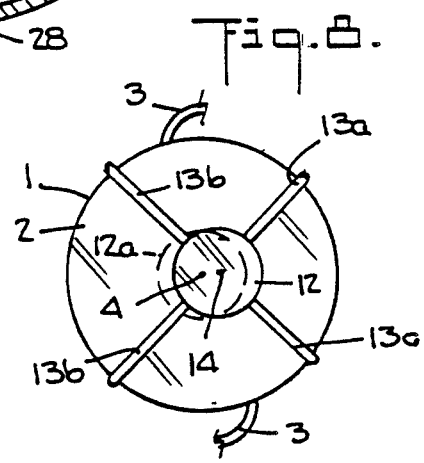
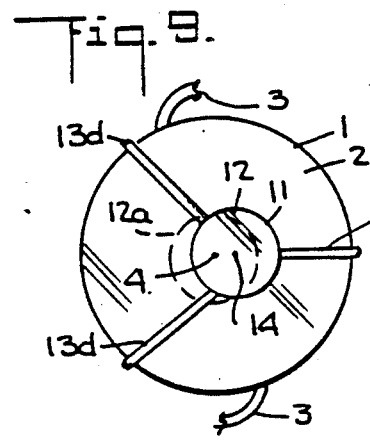
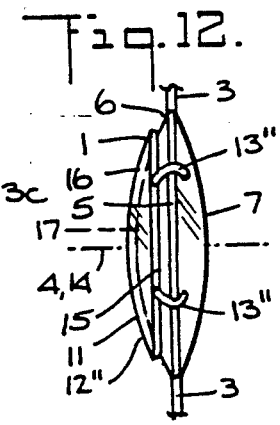
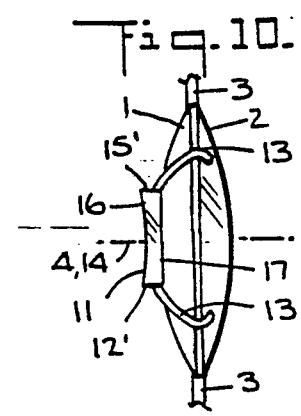

CLIP-ON OPTIC ASSEMBLY

FIELD AND BACKGROUND OF THE INVENTION

The present invention relates to a clip-on optic assembly, and more particularly to such an assembly which is capable of being clipped in situ onto a previously implanted artificial intraocular lens to change the optical characteristics thereof without having to remove the implanted lens from the eye, by insertion of the assembly through an incision into the eye and clipping it onto the implanted lens.

A recent innovation in the intraocular lens field is a new system intraocular lens whose lens body has a small central "high-minus" lens portion of approximately 2 mm diameter, surrounded by a peripherally extending, much more "positive" lens portion (J Cataract Refrac Surg, 14:421–430, July, 1988).

This new system intraocular lens is intended for patients with severe macula degeneration, as it allows the patient to see normally, by viewing through the peripherally extending portion, objects that are at a distance. On the other hand, for close vision, e.g. reading, eyeglasses having a compensating "plus" lens are worn by the user, the combination of the "plus" lens of the eyeglasses and the "high-minus" central lens portion of the intraocular lens together forming a structure of optical characteristics resembling those of a telescope for producing a magnified image on the retina.

However, patients who already have an implanted intraocular lens can only avail themselves of this new system by removing the existing implanted lens and replacing it with one having such a "high-minus" central portion. Due to tissue growth around the haptics or other position fixation means used to maintain the already implanted lens in the eye, as well as adhesion of eye tissue to other portions of the implant, especially where that lens has been implanted for an extended period of time, its removal and replacement involves relatively major and complex surgery and the risk of loss of vision.

U.S. Pat. No. 4,769,035, issued Sep. 6, 1988, to Kelman shows an artifical lens formed of a predetermined shape optic having a concave posterior surface corresponding to the anterior surface of the natural lens when the latter is in its flattest condition, and opposed haptics, adapted to seat in the surrounding tissue of the eye, to position the artificial lens, upon insertion through an incision into the eye, with its posterior surface seated directly against the anterior surface of the natural lens which remains in place and is not removed from the eye. The artificial lens cooperates with the natural lens for correcting conditions such as myopia and hyperopia.

U.S. Pat. No. 4,585,456, issued Apr. 29, 1986, to Blackmore also shows an artificial lens having haptics or the like, adapted to seat in the surrounding tissue of the eye, for locating the conforming posterior side of the artificial lens against the natural lens for correcting an eyesight condition.

It would be desirable to provide the benefits of the aforesaid new system intraocular lens having a "high-minus" central lens portion surrounded by a more "positive" peripheral lens portion, or other optical characteristic modifying benefits, to a patient already having an implanted intraocular lens, without subjecting the patient to removal of the latter and its replacement by such a new system intraocular lens, or to the risks of major or complex surgery.

SUMMARY OF THE INVENTION

An object of this invention is to provide a clip-on optic assembly of construction facilitating its clipping in situ onto a previously implanted artificial intraocular lens to change the optical characteristics thereof without having to remove it from the eye, and an associated minimum risk method for insertion of the assembly through an incision into the eye and facilitated clipping thereof onto the implanted lens, and to position the optical axis of the assembly lens body in selective axial relation to the implanted lens optical axis and the optical axis of the pupil of the eye.

Another object of this invention is to provide a kit comprising an inventory of a series of such assemblies having clip members of different size extending from the lens body to clip the same onto the implanted lens so as to position the lens body optical axis in eccentric axial relation to the implanted lens optical axis and substantially concentric axial relation to the optical axis of the pupil of the eye, as where the implanted lens has become decentered in the eye and its optical axis is not concentric to the pupil axis.

According to this invention, a clip-on optic assembly is provided, which is capable of being clipped in situ onto a previously implanted intraocular lens to change the optical characteristics thereof without having to remove the implanted lens from the eye, and without having to seat additional haptics in the eye tissue.

The optic assembly comprises a lens body, and a plurality of resilient clip members extending from the lens body in spaced apart relation to each other and outwardly terminating in corresponding gripping clips capable of manipulation for gripping the peripheral edge portion of the implanted lens to clip in situ the optic assembly thereon. At least one clip is in the form of a bent end which is sufficiently resilient to permit temporary unbending sufficiently for its local displacement over and across the adjacent peripheral edge portion of the implanted lens to grip the clip thereon.

In particular, the lens body may have a selectively smaller peripheral size than that of the implanted lens and a posterior surface shaped to correspond substantially to the anterior surface of the implanted lens in the region where the lens body and implanted lens overlap for mounting the assembly on the anterior surface of the implanted lens. The lens body may have a diameter for instance of about 2 mm.

Alternatively, the lens body may have a peripheral size corresponding substantially to the peripheral size of the implanted lens and a posterior surface shaped to correspond sufficiently to the anterior surface of the implanted lens for mounting the assembly on the anterior surface of the implanted lens while selectively modifying the optical characteristics of the implanted lens to correct an optical defect or deficiency thereof, e.g. it may be that it is discovered after implantation of an intraocular lens that a lens body with an incorrect or improper power was erroneously implanted and correction of the power is desired.

Desirably, the clip members are sufficiently resilient to permit temporary flexing of adjacent clip members toward each other to facilitate insertion of the assembly through a minimum size incision into the eye, i.e. of size corresponding generally to the lens body diameter.

According to an advantageous feature, the clips are disposed at concordantly selected respective radial distances from the optical axis of the lens body for maintaining that axis in substantially concentric, or alternatively slightly eccentric, relation to the optical axis of the implanted lens upon clipping the assembly thereon.

In the case of such eccentric relationship of the two optical axes, for instance, four clip members may be provided, of which two adjacent clip members ae slightly shorter in length than the remaining two clip members, or alternatively three clip members may be provided, of which one clip member is slightly shorter in length than the remaining two clip members.

Favorably, in this regard, a kit may be provided in the form of an inventory of a series of optic assemblies, such as one having four such clip members in which the two shorter clip members of the series of optic assemblies differ in length from one assembly to the next in the series by an increment of about 0.5 mm, or alternatively one having three such clip members in which the one shorter clip member of the series of optic assemblies differs in length from one assembly to the next in the series by such an increment of about 0.5 mm.

This invention also contemplates the combination of the optic assembly clipped in situ onto a previously implanted intraocular lens, as well as the corresponding method of providing this combination which involves inserting the optic assembly through an incision into the interior of an eye containing a previously implanted intraocular lens, and clipping the assembly in situ onto the implanted lens.

The clipping is effected by manipulating the clips of all but a last of the clip members to grip the clips onto the adjacent peripheral edge portion of the implanted lens to stabilize the disposition of the assembly thereon, the last of the clip members having a clip in the form of an aforesaid bent end, and then manipulating the bent end clip of the last of the clip members onto the adjacent peripheral edge portion of the implanted lens by temporarily unbending the bent end sufficiently for its local displacement over and across the peripheral edge portion thereat to grip the clip thereon and thereby complete the clipping of the assembly in situ onto the implanted lens.

BRIEF DESCRIPTION OF THE DRAWINGS

Other objects of the invention will become apparent from the within specification and accompanying drawings, in which:

FIGS. 1 and 2 are schematic views of the anterior side, and end, respectively, of a prior art previously implanted intraocular lens, having a pair of diametrically opposed haptics in engagement with the adjacent tissue of the eye;

FIGS. 3 and 4 are schematic views of the anterior side, and end, respectively, of an optic assembly according to an embodiment of the invention;

FIGS. 5 and 6 are schematic views of the anterior side, and end, respectively, of the combination of the optic assembly of FIGS. 3-4 clipped onto the implanted lens of FIGS. 1-2, according to the invention;

FIG. 7 is a schematic sectional view of an eye showing the manner of inserting the optic assembly of FIGS. 3-4 via an incision for clip-on mounting in situ on the implanted lens of FIGS. 1-2 to form the combination of FIGS. 5-6;

FIGS. 8 and 9 are schematic views, similar to FIG. 5, of combinations of the implanted lens with four and three clip member containing assemblies, respectively, according to the invention, for providing an eccentric relation between the optical axes of these two parts;

FIG. 10 is a schematic view of another type optic assembly lens body mounted on the implanted lens to provide other optical characteristics for the resulting combination; and FIGS. 11–12 are schematic views of the anterior side and end, respectively, of a further full size, lens body embodiment according to the invention.

DESCRIPTION OF THE PREFERRED EMBODIMENTS

Referring to the drawings, and initially to FIGS. 1–2, a prior art previously implanted artificial intraocular lens 1 is shown, including an optic or lens body 2 having position fixation means such as a pair of opposed haptics 3 outwardly extending, e.g. generally radially, therefrom and seated against adjacent eye tissue 27 and 31 (shown in phantom) to implant lens 1 in the eye in the usual manner. Lens body 2 has a central optical axis 4, a circular peripheral edge 5, and anterior and posterior surfaces 6 and 7, respectively, which for instance may be of generally convex shape.

As shown in FIGS. 3–4, according to the invention, a miniature clip-on optic assembly 11 is provided, including a generally central optic or lens body 12 of miniature size, e.g. of smaller peripheral size than that of lens body 2, such as one of about 2 mm diameter as compared to a diameter of about 6 mm for lens body 2, and a plurality of resilient clip members 13, e.g. formed as thin strands, such as four clip members as shown, extending, preferably generally radially, from lens body 12 in spaced apart relation to each other. Like lens body 2 of lens 1, lens body 12 of assembly 11 has a central optical axis 14, a circular peripheral edge 15, and anterior and posterior surfaces 16 and 17, respectively.

However, while anterior surface 16 is of generally convex shape, in this instance posterior surface 17 is of generally concave shape and is specifically configured to correspond substantially to the counterpart shape of anterior surface 6 of lens 1. In any case, lens body 12 is provided with an overall shape and size specifically adapted to change the existing optical characteristics of lens body 2 in desired manner when clipped thereon, as shown in FIGS. 5–6.

To achieve in situ clipping of assembly 11 onto implanted lens 1 within the eye, clip members 13 outwardly terminate at their free ends in corresponding gripping clips 18 which are constructed so as to be capable of individual local manipulation within the eye for gripping the adjacent peripheral edge 5 of lens 1 to clip assembly 11 thereon in facilitated manner.

For this purpose, as shown in FIGS. 4 and 7, at least one and preferably all of the clips 18 are in the form of a bent or bended end 19, e.g. of open hook shape, which is sufficiently resilient to permit temporary unbending or distention sufficient for local displacement thereof, once inserted into the eye interior, over and across the adjacent peripheral edge 5 of lens 1 to grip the clip 18 thereon.

As shown in FIG. 7, the eyeball 21 includes the cornea 22 and the iris 23, the latter forming the adjustable central pupil opening 24 that separates the anterior chamber 25 from the posterior chamber 26. The previously implanted lens 1 is typically positioned with one haptic in the capsule portion 27, and the other haptic in the ciliary sulcus 31, after extracapsular removal of the natural eye lens (not shown) by known surgical procedures, capsule portion 27 being located by the zonules or suspensory ligament and fibers 28, attached to its periphery, in posterior chamber 26. For example, lens 1 may be disposed in front of capsule portion 27 with its posterior surface 7 substantially adjacent but spaced from the posterior wall 29 and its haptics 3 in contact with the peripheral groove or cul-de-sac 30 and the ciliary sulcus 31, respectively.

For combining assembly 11 with the already implanted intraocular lens 1, to change the optical characteristics of the latter, assembly 11 is preferably inserted through a minimum size corneal incision 22a (FIG. 7), i.e. of size or length just sufficient for lens body 12 to pass therethrough, e.g. about 2 mm in length for a lens body 12 of about 2 mm diameter, so as to minimize trauma to the patient.

As shown in phantom in FIG. 7, this may be done by passing two adjacent clip members 13 through incision 22a, e.g. temporarily flexing them together to facilitate their insertion in compact condition by "snaking" them therethrough, next passing optic 12 through incision 22a, and then passing the remaining two adjacent clip members 13 in flexed together compact condition therethrough. Once assembly 11 is inserted in the eye, for example three clip members 13 may be manipulated to slidingly engage their clips 18 grippingly onto the adjacent portions of peripheral edge 5 of lens 1 via their bent ends 19, to stabilize the disposition of assembly 11 thereon with minimum chance of disturbing the implanted lens while leaving free the bent end 19 of the last clip member 13.

Finally, as also shown in phantom in FIG. 7, the surgeon can manipulate the bent end 19 of that last clip member 13 with facility onto its adjacent portion of peripheral edge 5, by temporarily unbending that bent end 19 sufficiently for its local displacement over and across peripheral edge 5 to grip the last clip 18 thereon, to complete the clipping of assembly 11 in situ onto lens 1 with minimum chance of disturbing the intact integrity of lens 1 in capsule portion 27.

It will be noted that clip members 13 extend from the periphery of lens body 12, e.g. at peripheral edge 15, in peripherally spaced relation to each other, and terminate individually at their outer ends in a clip 18 at a selective radial distance from optical axis 14 for engaging peripheral edge 5 of lens 1 to clip assembly 11 thereon, such that optical axis 14 is in a selective axial relation to optical axis 4.

As shown in FIGS. 5–6, when these two parts are combined, these axes 4 and 14 may be selectively arranged to coincide. This is the normal case encountered. However, there are instances in which it is found that the implanted lens is not concentric with the optical axis of the pupil of the eye, but rather is axially offset slightly therefrom so as to be eccentric thereto. This is because implanted intraocular lenses sometimes shift within the eye and become decentered. Consequently, the optical axis of the implant lens becomes decentered from the optical axis of the pupil.

According to an advantageous feature of the invention, such decentering and resulting eccentric condition of these two optical axes can be corrected by providing assembly 11 with clip members 13 of unequal (radial) length to compensate for this difference so as to position optical axis 14 slightly eccentric to optical axis 4 yet substantially concentric to the optical axis of pupil 24.

Thus, as shown in FIG. 8, by forming assembly 11 with two adjacent clip members 13a correspondingly shorter than the remaining two clip members 13b, then upon clipping assembly 11 in situ on lens 1, instead of lens body 12 being positioned centrally and coaxially on lens body 1, as shown in phantom in FIG. 8, lens body 12 is slightly offset so that its axis 14 is selectively slightly eccentric to axis 4 but maintained substantially concentric to the axis of pupil 24 (not shown).

FIG. 9 shows a similar axially offset arrangement to that of FIG. 8, but with assembly 11 having three spaced apart clip members, clip member 13c being shorter than the remaining two clip members 13d. Thus, upon clipping assembly 11 on lens 1, lens body 12 will be slightly offset so that its axis 14 is selectively slightly eccentric to axis 4 but maintained substantially concentric to the axis of pupil 24.

FIG. 10 shows an alternate embodiment in which lens body 12' of assembly 11 has a concave anterior surface 16' and a concave posterior surface 17' thereby forming a flat side wall type periphery 15'. Lens body 12' is used to obtain a different type change in the optical characteristics of lens body 2 according to the invention, as the artisan will appreciate.

FIGS. 11–12 show a further embodiment in which the only significant difference is that lens body 12" is substantially equal, or almost equal, in diameter size and peripheral size to lens body 2, such that much shorter clips 13" are used to clip assembly 11 onto lens body 2, with its concave posterior surface 17 in substantially conforming surface contact with anterior surface 6 of lens body 2, depending on the resultant optical characteristics sought for the combination system.

Specifically, this large or full diameter or peripheral size lens body 12" is used for instance to correct an improper or incorrect power, i.e. diopter, of already implanted lens body 2, and for this purpose is sized and shaped for covering substantially the entire anterior surface 6 of the in situ implanted intraocular lens 1. For example, for an implanted intraocular lens of 4–6 mm diameter, lens body 12" may have a corresponding diameter of about 3–5 mm.

Since the optical characteristics of lens body 2 are already known, i.e. consequent the previous procedures for preparing and implanting intraocular lens 1, lens body 12" can be fabricated to provide it with optical characteristics designed to compensate for the existing defect, e.g. by correcting an improper power of lens body 2, such that the resulting combination will obviate the defect.

It will be understood that, depending on the optical and other characteristics sought, lens body 12 may be provided of any suitable conforming shape and size for use with an implanted lens 1 having any given shape and size lens body 2, e.g. one with a circular, elliptical or rectangular shape, or in which anterior and posterior surfaces 6 and 7 are both convex or concave, or one is convex and the other concave.

For instance, the comparatively small diameter size or small peripheral size lens body, e.g. lens body 12 of FIG. 5 may be provided with optical characteristics relative to lens body 2 of the implanted intraocular lens 1 to provide a resultant optical system in which lens body 12 serves as a bifocal add-on optic, e.g. a high "plus" diopter optic, such that lens body 12 and the central portion of lens body 2 together provide for near vision or close reading vision while the peripheral portion of lens body 2 which is not covered by lens body 12 separately provides for far vision or distant vision.

The above arrangements enable axis 14 to be maintained in a selective axial relation to axis 4 and inherently also in a corresponding relation to the axis of the pupil, i.e. by providing the radial distances of clips 13 from axis 14 selectively concordantly such that axis 14 is adapted to be substantially concentric to, or alternatively slightly eccentric to, axis 4 upon clipping assembly 11 on lens 1. In the latter case, clip members 13 are of concordantly unequal length for positioning axis 14 selectively slightly eccentric to axis 4.

Although the above embodiments show four or three clip members, it will be understood that two opposed clip members, or more than four clip members, may be provided, as desired, so long as they achieve proper gripping via their clips onto the implanted lens, whether the clip members are of equal, or concordantly selected unequal, length for the stated purposes.

According to a further advantageous feature, a kit may be provided which comprises an inventory of a series of appropriate differential size optic assemblies containing shorter and longer clip members, e.g. as shown in FIG. 8 or FIG. 9.

Specifically, where there are four clip members, of which two adjacent clip members 13a are slightly shorter in length than the other two clip members 13b, the two shorter clip members 13a of the series of optic assemblies in the kit may differ in length from one assembly to the next in the series, e.g. by an increment of about 0.5 mm. Likewise, where there are three clip members, of which one clip member 13c is slightly shorter in length than the other two clip members 13d, the shorter clip member 13c of the series of optic assemblies in the kit may also differ in length from one assembly to the next in the series, e.g. by such an increment of about 0.5 mm.

By use of an inventory of assemblies 11 with a length difference from one to the next of shorter clip members 13a (FIG. 8), or shorter clip member 13c (FIG. 9), or the like, e.g. in 0.5 mm increments, the surgeon can select a suitably dimensioned assembly, depending on the amount of decentering found, so that the assembly will have its optical center in general alignment with the optical axis of the pupil even though it is clipped onto a decentered implanted lens.

This is because the particular assembly 11 from the kit inventory will be selected on the basis that its differentially sized clips will locate lens body 12 on lens body 2 such that axis 14 of lens body 12 will be maintained in optimum precise manner in selective eccentrically offset decenter-compensating relation to axis 4 of decentered lens body 2 yet in substantially coaxial relation to the axis of the pupil 24 of the eye.

Thus, compared to the need heretofore for replacing a previously implanted intraocular lens in those patients suffering from macula degeneration or the like, with a new intraocular lens having a small central lens portion in the form of a high minus lens surrounded by a peripherally extending, much more positive lens portion, to correct for such impairment, using as needed plus lens type eyeglasses, this invention achieves the desired end without removing anything.

Instead, by way of this invention, assembly 11 may include such a high minus type optic in the form of lens body 12, for independent insertion into the eye and in-situ clipping thereof via gripping clips 18 of haptic-like clip members 13 onto the previously implanted, e.g. positive or plus type, lens 1 to change its optical characteristics to replicate substantially the unitary construction of an otherwise replacement high minus lens containing new system of the aforesaid known type, but without the drawbacks of the procedure heretofore required.

For example, if the previously implanted lens 1 has a lens body 2 in the form of a "plus 10" lens, and the clip-on lens body 12 constitutes a "minus 60" lens, the resulting combination in situ in the eye according to the invention will provide a "minus 50" lens system. With this combination, the user can experience normal distance vision through the peripheral portions of the previously implanted lens body 2, while excellent close vision will be achieved at the central portion of the optic, provided by the combination of lens body 12 and the central portion of lens body 2, in further combination in the usual way with high plus spectacles or eyeglasses, e.g. having a "plus 30" lens, worn for reading and the like.

For optimum efficiency of the combination optical system of assembly 11 clipped onto lens 1, posterior surface 17 of lens body 12 is specifically shaped to conform substantially to the counterpart shape of anterior surface 6 of lens body 2 sufficiently to provide an effective continuous, generally smooth and even, coextensive surface to surface abutting contact interface relation therebetween, suitably essentially without the existence of any intervening void space (cf. FIGS. 6, 7 and 10).

This coextensive conforming contact interface relation between posterior surface 17 and anterior surface 6 will be taken into account in fashioning the shape and profile of lens body 12, not only where lens 1 is coaxial with the axis of pupil 24 in the eye but also where lens 1 is decentered relative to the axis of pupil 24.

Thus, in an appropriate case, assuming there is no space between the coextensive portions of posterior surface 17 of lens body 12 and anterior surface 6 of implant lens 1, the approximate lens power, in the eye, of these two lenses in combination, for instance, may be from about $-45$ to $-65$ diopters, representing the additive power of both lens body 2 of the original implant lens 1 and lens body 12 of clip-on assembly 11, as where lens body 2 is a $+20$ diopters lens and lens body 12 is a lens of from about $-65$ to $-85$ diopters.

This will correspondingly produce (a) a total power in the eye of $-45$ diopters where lens body 12 is a $-65$ diopters lens ($+20$ minus $-65 = -45$, at a separation value of 85 diopters between the two lenses), or (b) a total power in the eye of $-65$ diopters where lens body 12 is a $-85$ diopters lens ($+20$ minus $-85 = -65$, at a separation value of 105 diopters between the two lenses).

When the combination of these two lenses in the aqueous humor in the eye is used with high plus spectacles, e.g. a $+25$ to $+35$ diopters spectacle lens in the air, the overall combination of the spectacles, cornea and both lens body 2 of implanted lens 1 and lens body 12 of assembly 11 taken together, will result in a Galilean telescope type optical system which may advantageously have a magnification of 2× to 4×, e.g. for wide field of view, magnified image, "close vision" reading and the like purposes.

On the other hand, when the spectacles are not being worn, the peripheral portion of lens body 2 will be used for normal vision, e.g. for normal full field of view, unmagnified image, "distant vision" walking and the like purposes.

In this regard, for example, where lens body 12 is a high minus diopter lens and lens body 2 is a normal plus diopter lens, e.g. a +20 diopter lens, the optical nature of lens body 12 in relation to lens body 2 is such that, when spectacles are not worn, the high minus effect of lens body 12 causes a condition of pronounced hyperopia (far-sightedness) which inhibits the formation of a retinal image, and thus inhibits any tendency toward double vision, whereas the positive peripheral portion of lens body 2, which is inherently of predominantly larger area than that of lens body 12 (cf. FIG. 5), forms a retinal image in the normal way for "distant vision", e.g. for walking and the like purposes, substantially unhindered by the presence of lens body 12.

Of course, it will be appreciated that the invention is not limited to a "high minus" lens body 12, but rather lens body 12 may be of any selective diopter value for use with a given diopter value lens body 2 of an already implanted lens 1, whereby to modify the optical characteristics of the latter as desired.

Indeed, where the small diameter size optic (e.g. lens body 12 of FIG. 5) serves as a bifocal add-on clip assembly system, the resultant combination may be used advantageously in appropriate cases without the need for complemental spectacle lenses.

Of course, the actual convex or concave shape and corresponding plus or minus diopter value characteristics assigned to a given clip-on optic of assembly 11, will depend upon the existing optical characteristics of the implanted intraocular lens and the nature of the modification thereof intended to be produced by combining the add-on clip assembly therewith according to the invention. These factors are well known to the attending ophthalmologist.

It will be understood that the previously implanted lens need not be located in the posterior chamber as shown in FIG. 7, but instead may be located at any site in the eye such as anteriorly of the iris in the anterior chamber or in a different disposition in the posterior chamber than that shown in FIG. 7, and the assembly may be clipped in situ thereon in equally facilitated manner to achieve such change of the optical characteristics of the previously implanted lens.

Lens body 12 may be made of suitable resilient material such as resilient plastic material, e.g. polymethylmethacrylate (PMMA) or PROLENE (a polypropylene material), or of suitable rigid material such as glass.

Clip members 13 may be made of suitable resilient material such as resilient plastic material, e.g. PMMA or PROLENE, preferably formed as "springy" pliable strands having suitable properties, such as shape "memory", to achieve both the stated temporary unbending of the bent end portion of the clips and permanent gripping or clamping action of the stated type thereafter. Clip members 13 may be integral with or connected, e.g. rigidly, to lens body 12.

In particular, it will be noted that by providing lens body 12 of glass, which normally has a higher index of refraction than plastic, it may be made thinner than if provided of plastic such as PMMA, in which case a rigid connection will be required between clip members 13 and glass lens body 12 to facilitate the clip-on action, whereas by providing lens body 12 of plastic such as PMMA, it may be formed with clip members 13 of PMMA as well, in which case an integral connection there-between may be conveniently utilized for such purposes, thereby providing a monolithic construction.

In any event, lens body 12 will be formed in appropriate shape and size of suitable light-focusing material having the desired optical characteristics, with all materials used for assembly 11 being compatible with the internal eye environment, and thus non-toxic.

It will be appreciated that the foregoing specification and accompanying drawings are set forth by way of illustration and not limitation of the present invention, and that various modifications and changes may be made therein without departing from the spirit and scope of the present invention which is to be limited solely by the scope of the appended claims.

What is claimed is:

1. A clip-on optic assembly, capable of being clipped in situ onto a previously implanted intraocular lens to change the optical characteristics thereof without having to remove the implanted lens from the eye, which comprises
    a lens body, and
    a plurality of resilient clip members extending from the lens body in spaced apart relation to each other and outwardly terminating in corresponding gripping clips capable of manipulation for gripping the peripheral edge portion of the implanted lens to clip in situ the optic assembly thereon, at least one clip being in the form of a bent end which is sufficiently resilient to permit temporary unbending sufficiently for local displacement thereof over and across the adjacent peripheral edge portion of the implanted lens to grip the clip thereon.

2. Assembly of claim 1 wherein the lens body has a selectively smaller peripheral size than the peripheral size of the implanted lens and a posterior surface shaped to correspond substantially to the anterior surface of the implanted lens in the region where the lens body and implanted lens overlap for mounting the assembly on the anterior surface of the implanted lens.

3. Assembly of claim 2 wherein the lens body has a diameter of about 2 mm.

4. Assembly of claim 1 wherein the lens body has a peripheral size corresponding substantially to the peripheral size of the implanted lens and a posterior surface shaped to correspond sufficiently to the anterior surface of the implanted lens for mounting the assembly on the anterior surface of the implanted lens while selectively modifying the optical characteristics of the implanted lens to correct an optical defect thereof.

5. Assembly of claim 4 wherein the lens body has a diameter of about 3-5 mm.

6. Assembly of claim 1 wherein the lens body is shaped to provide it with optical characteristics for producing a resultant bifocal optical system when mounted on the implanted lens.

7. Assembly of claim 1 wherein the clip members are sufficiently resilient to permit temporary flexing of adjacent clip members toward each other to facilitate insertion of the assembly through a minimum size incision into the eye.

8. Assembly of claim 1 wherein the lens body has an optical axis and the clips are disposed at concordantly selected respective radial distances therefrom for maintaining the lens body optical axis in substantially concentric relation to the optical axis of the implanted lens upon clipping the assembly thereon.

9. Assembly of claim 1 wherein the lens body has an optical axis and the clips are disposed at concordantly selected respective radial distances therefrom for maintaining the lens body optical axis in selective slightly eccentric relation to the optical axis of the implanted lens upon clipping the assembly thereon.

10. Assembly of claim 9 wherein four clip members are provided, of which two adjacent clip members are slightly shorter in length than the remaining two clip members.

11. Assembly of claim 9 wherein three clip members are provided, of which one clip member is slightly shorter in length than the remaining two clip members.

12. A kit comprising an inventory of a series of optic assemblies of claim 10, wherein the two shorter clip members of the series of optic assemblies differ in length from one assembly to the next in the series by an increment of about 0.5 mm.

13. A kit comprising an inventory of a series of optic assemblies of claim 11, wherein the one shorter clip member of the series of optic assemblies differs in length from one assembly to the next in the series by an increment of about 0.5 mm.

14. Combination of an optic assembly of claim 1 and an intraocular lens adapted to be implanted into the interior of an eye, said optic assembly adapted to be clipped in situ onto the intraocular lens after previously implanting said intraocular lens.

15. Combination of claim 14 wherein the implantable lens has a plus type lens body and the assembly has a high minus type lens body.

16. Combination of claim 14 wherein the lens body has a selectively smaller peripheral size than the peripheral size of the implantable lens and a posterior surface shaped to correspond substantially to the anterior surface of the implantable lens in the region where the lens body and implantable lens overlap for mounting the assembly on the anterior surface of the implantable lens.

17. Combination of claim 14 wherein the implantable lens has an optical defect, and the lens body has a peripheral size corresponding substantially to the peripheral size of the implantable lens and a posterior surface shaped to correspond sufficiently to the anterior surface of the implantable lens for mounting the assembly on the anterior surface of the implantable lens while selectively modifying the optical characteristics of the implantable lens to correct the optical defect thereof.

18. Combination of claim 14 wherein the lens body is shaped to provide it with optical characteristics for producing a resultant bifocal optical system when mounted on the implantable lens.

19. Method of providing the combination of claim 14, comprising
inserting the optic assembly through an incision into the interior of an eye containing said intraocular lens previously implanted into the interior of the eye, and
clipping the assembly in situ onto the previously implanted lens, by manipulating the clips of all but a last of the clip members to grip the clips onto the adjacent peripheral edge portion of the implanted lens to stabilize the disposition of the assembly thereon, said last of the clip members having a clip in the form of said bent end, and then manipulating the bent end clip of the last of the clip members onto the adjacent peripheral edge portion of the implanted lens by temporarily unbending the bent end sufficiently for local displacement thereof over and across said peripheral edge portion thereat to grip the clip thereon and thereby complete the clipping of the assembly in situ onto the implanted lens.

20. Method of claim 19 wherein the clips are disposed at concordantly selected respective radial distances from the optical axis of the lens body of the assembly such that the lens body optical axis is maintained in substantially concentric relation to the optical axis of the implanted lens upon clipping the assembly thereon.

21. Method of claim 19 wherein the clips are disposed at concordantly selected respective radial distances from the optical axis of the lens body of the assembly such that the lens body optical axis is maintained in selective slightly eccentric relation to the optical axis of the implanted lens and in substantially concentric alignment with the optical axis of the pupil of the eye upon clipping the assembly on the implant lens.

22. Method of claim 19 wherein the implanted lens has a plus type lens body and the assembly has a high minus type lens body.

23. Method of claim 22 wherein the implanted lens plus type lens body has a diopter value for providing normal image size distant vision as for walking and the like purposes, when spectacles are not worn, and the assembly high minus type lens body has a diopter value selected, relative to the diopter value of the implant lens plus type lens body, for providing magnified image size close vision as for reading and the like purposes, when complemental diopter value plus type lens body containing spectacles are worn.

24. Method of claim 19 wherein the lens body has a selectively smaller peripheral size than the peripheral size of the implanted lens and a posterior surface shaped to correspond substantially to the anterior surface of the implanted lens in the region where the lens body and implanted lens overlap for mounting the assembly on the anterior surface of the implanted lens.

25. Method of claim 19 wherein the implanted lens has an optical defect, and the lens body has a peripheral size corresponding substantially to the peripheral size of the implanted lens and a posterior surface shaped to correspond sufficiently to the anterior surface of the implanted lens for mounting the assembly on the anterior surface of the implanted lens while selectively modifying the optical characteristics of the implanted lens to correct the optical defect thereof.

26. Method of claim 19 wherein the lens body is shaped to provide it with optical characteristics for producing a resultant bifocal optical system when mounted on the implanted lens.

27. An attachment optic assembly, capable of being attached in situ onto a previously implanted intraocular lens to change the optical characteristics thereof without having to remove the implanted lens from the eye, which comprises
a lens body, and
a plurality of attachment members extending from the lens body in spaced apart relation to each other and outwardly terminating in corresponding attachment portions defining attachment means for attaching the lens body to the implanted lens to locate in situ the optic assembly thereon.

* * * * *